US011518976B2

(12) United States Patent
Kawashima et al.

(10) Patent No.: US 11,518,976 B2
(45) Date of Patent: Dec. 6, 2022

(54) METHOD FOR PRODUCING DOUBLE-STRANDED RNA-RICH LACTIC ACID BACTERIUM, AND SAID LACTIC ACID BACTERIUM

(71) Applicant: Kikkoman Corporation, Chiba (JP)

(72) Inventors: Tadaomi Kawashima, Chiba (JP); Naho Ikari, Chiba (JP); Hiroshi Kawamoto, Chiba (JP)

(73) Assignee: KIKKOMAN CORPORATION, Chiba (JP)

( * ) Notice: Subject to any disclaimer, the term of this patent is extended or adjusted under 35 U.S.C. 154(b) by 213 days.

(21) Appl. No.: 16/612,103

(22) PCT Filed: May 11, 2018

(86) PCT No.: PCT/JP2018/018392
§ 371 (c)(1),
(2) Date: Nov. 8, 2019

(87) PCT Pub. No.: WO2018/207924
PCT Pub. Date: Nov. 15, 2018

(65) Prior Publication Data
US 2020/0115673 A1    Apr. 16, 2020

(30) Foreign Application Priority Data

May 12, 2017  (JP) .............................. JP2017-095947

(51) Int. Cl.
C12N 1/20        (2006.01)
A23L 33/135      (2016.01)
C12N 15/74       (2006.01)
A23K 10/18       (2016.01)

(52) U.S. Cl.
CPC ................ *C12N 1/20* (2013.01); *A23K 10/18* (2016.05); *A23L 33/135* (2016.08); *C12N 15/746* (2013.01); *A23V 2002/00* (2013.01); *A23Y 2220/49* (2013.01); *A23Y 2280/15* (2013.01); *C12N 2500/02* (2013.01)

(58) Field of Classification Search
CPC .... C12N 1/20; C12N 2500/02; C12N 15/117; A23K 10/18; A23L 33/135; A23V 2002/00; A23Y 2220/49; A23Y 2280/15
See application file for complete search history.

(56) References Cited

U.S. PATENT DOCUMENTS

| | | | |
|---|---|---|---|
| 2007/0071737 A1 | 3/2007 | Koga | |
| 2011/0159552 A1 | 6/2011 | Masuda et al. | |
| 2011/0256611 A1 | 10/2011 | Kawashima et al. | |

FOREIGN PATENT DOCUMENTS

| | | |
|---|---|---|
| CN | 1625345 | 6/2005 |
| CN | 101796187 | 8/2010 |
| EP | 2 169 057 | 3/2010 |
| JP | 9-238647 | 9/1997 |
| JP | 10-139674 | 5/1998 |
| JP | 2008-301812 | 12/2008 |
| JP | 2010-252641 | 11/2010 |
| JP | 5099649 | 12/2012 |
| JP | 2014-50325 | 3/2014 |
| JP | 2014-140330 | 8/2014 |
| JP | 2015-92841 | 5/2015 |
| WO | 03/082027 | 10/2003 |
| WO | 2009/005123 | 1/2009 |
| WO | 2009/005124 | 1/2009 |

OTHER PUBLICATIONS

Kuwahara et al., Nucleic Acids Symposium Series, 2007, No. 51, p. 413-414.*
Kawashima et al., Immunity. Jun. 27, 2013;38(6):1187-97. doi: 10.1016/j.immuni.2013.02.024. Epub Jun. 20, 2013. PMID: 23791646, and "Supplemental Information" pp. 1-13.*
BioNumbers; B10NUMB3R5, The database of useful Biological Numbers retrieved from https://bionumbers.hms.harvard.edu/bionumber.aspx?s=n&v=2&id=109837 on Nov. 3, 2021, 1 page.*
Extended European Search Report dated Jun. 5, 2020 in European Patent Application No. 18798729.2.
Thammasorn et al., "Probiotic bacteria (*Lactobacillus plantarum*) expressing specific double-stranded RNA and its potential for controlling shrimp viral and bacterial diseases", Aquaculture International, 2017, vol. 25, No. 5, pp. 1679-1692.
Kawashima et al., "Supplemental Information Double-Stranded RNA of Intestinal Commensal but not Pathogenic Bacteria Triggers Production of Protective Interferon-β", Immunity, 2017, vol. 38. Retrieved from the Internet: URL:https://ars.els-cdn.com/content/image/1-s2.0-S1074761313002409-mmc1.pdf on May 20, 2020. 14 pages.

(Continued)

*Primary Examiner* — Kade Ariani
(74) *Attorney, Agent, or Firm* — Wenderoth, Lind & Ponack, LLP (57) ABSTRACT

An object of the present invention is to provide a method for efficiently obtaining a lactic acid bacterium that is made to contain a large amount of double-stranded RNA; and a lactic acid bacterium having a high double-stranded RNA content obtained by the method. The object is achieved by: (1) a method for producing a double-stranded RNA-containing lactic acid bacterium, including a step of culturing a lactic acid bacterium under at least one condition of an aeration condition and a low-temperature condition lower than an optimum temperature, thereby obtaining the double-stranded RNA-containing lactic acid bacterium; (2) a double-stranded RNA-containing lactic acid bacterium, in which the content of double-stranded RNA is 2.0 times or more as compared with the content of double-stranded RNA when a bacterium of the same strain is cultured for the same culture time under an optimum temperature and non-aeration condition; or the like.

6 Claims, 4 Drawing Sheets

(56) References Cited

OTHER PUBLICATIONS

Kawashima et al., "Double-Stranded RNA of Intestinal Commensal but Not Pathogenic Bacteria Triggers Production of Protective Interferon-B", Immunity, 38: 1187-1197 (2013).
International Search Report, dated Jul. 24, 2018 in corresponding International Patent Application No. PCT/JP2018/018392.
Partial Supplementary European Search Report dated Mar. 11, 2020 in corresponding European Patent Application No. 18798729.2.
Office Action dated Oct. 10, 2022 in the corresponding Chinese patent application No. 201880031057.4.

\* cited by examiner

METHOD FOR PRODUCING DOUBLE-STRANDED RNA-RICH LACTIC ACID BACTERIUM, AND SAID LACTIC ACID BACTERIUM

TECHNICAL FIELD

The present invention relates to a method for producing a lactic acid bacterium having a high double-stranded RNA content, and the lactic acid bacterium.

BACKGROUND ART

It is known that in the innate immune cell response, immune cells such as dendritic cells or macrophages respond to an innate immune activator derived from a bacterium or a virus to produce an interferon or a cytokine, and thereafter an immune reaction occurs. The innate immune cell response is an infection defense mechanism that living organisms have in common, and is nonspecific, and therefore is characterized in that it responds quickly and effectively functions against many sources of infection.

Immune cells involved in the innate immune cell response cause an immune reaction generally through a Toll-like receptor (TLR). TLR is a class of proteins present in a cell membrane or an endosome, and recognizes an innate immune activator outside the cells and transmits the information inside the cells so as to lead to the production of a biologically active substance such as an interferon or a cytokine.

It is known that TLR3 which is one member of TLR recognizes viral double-stranded RNA and induces the activation of an interferon-$\beta$ promotor and the production of interferon-$\beta$ independently of MyD88. Interferon-$\beta$ activates dendritic cells and induces the production of an inflammatory cytokine such as interleukin-12. Further, interleukin-12 induces the differentiation of naive T cells into helper T type 1 (Th1) cells, and the innate immune cell response is thus established.

The innate immune cell response through TLR3 by viral double-stranded RNA brings about the activation or suppression of an immune reaction and can control the innate immunity to be normal. However, utilization of a virus itself as double-stranded RNA for controlling the innate immunity is not realistic in terms of safety.

Therefore, it is considered to utilize a microorganism that does not adversely affect human bodies as a double-stranded RNA-containing material or utilize double-stranded RNA isolated from the microorganism in place of viral double-stranded RNA. In particular, if a lactic acid bacterium or the like having the experience of being eaten is used as the microorganism that does not adversely affect human bodies, the innate immunity can be maintained favorable on a daily basis. For example, Patent Literature 1 describes a lactic acid bacterium which is made to produce double-stranded RNA in the bacterial cells under a stress condition with a salt, and a method for producing the same.

CITATION LIST

Patent Literature

Patent Literature 1: Japanese Patent No. 5099649

SUMMARY OF INVENTION

Technical Problem

However, according to a study conducted by the present inventors, there is a case where proliferation inhibition is prominently exhibited due to the stress condition with a salt among lactic acid bacteria, and as a result, it is difficult to obtain a large amount of lactic acid bacteria containing double-stranded RNA. In this manner, depending on the lactic acid bacterium, prominent proliferation inhibition occurs due to the type of stress condition, and as a result, double-stranded RNA cannot be efficiently contained.

Accordingly, an object of the present invention is to provide a method for efficiently obtaining a lactic acid bacterium that is made to contain a large amount of double-stranded RNA, and a lactic acid bacterium having a high double-stranded RNA content obtained by the method.

Solution to Problem

The present inventors made intensive studies for achieving the above object, and as a result, they surprisingly succeeded in increasing the content of double-stranded RNA in a lactic acid bacterium by culturing the lactic acid bacterium that is generally cultured under a non-aeration condition under an aeration condition. However, the present inventors found that it is difficult to maintain the amount of double-stranded RNA in bacterial cells of the lactic acid bacterium and particularly, the amount of double-stranded RNA easily decreases with the passage of culture time.

In view of the above, they further conducted trial and error and thus found that by culturing a lactic acid bacterium under a low-temperature condition in addition to an aeration condition, the proliferation rate of the lactic acid bacterium can be reduced, and a decrease in the content of double-stranded RNA in bacterial cells can be mitigated accompanying this. Then, they surprisingly succeeded in obtaining a double-stranded RNA-containing lactic acid bacterium at an industrial scale by combining an aeration condition and a low-temperature condition. These findings and successful examples are brought about for the first time by the present inventors. Then, the present invention is an invention completed based on these findings and successful examples.

Therefore, according to one embodiment of the present invention, a lactic acid bacterium, a composition, and a method of embodiments shown in the following (1) to (12) are provided.

(1) A method for producing a double-stranded RNA-containing lactic acid bacterium, including a step of culturing a lactic acid bacterium under at least one condition of an aeration condition and a low-temperature condition lower than an optimum temperature, thereby obtaining the double-stranded RNA-containing lactic acid bacterium.

(2) The method for producing a double-stranded RNA-containing lactic acid bacterium according to (1), including a step of culturing a lactic acid bacterium under an aeration condition and a low-temperature condition lower than an optimum temperature, thereby obtaining the double-stranded RNA-containing lactic acid bacterium.

(3) The production method according to (1) or (2), wherein the content of double-stranded RNA in the double-stranded RNA-containing lactic acid bacterium is 2.0 times or more as compared with the content of double-stranded RNA when a bacterium of the same strain is cultured for the same culture time under an optimum temperature and non-aeration condition.

(4) The production method according to any one of (1) to (3), wherein the content of double-stranded RNA in the double-stranded RNA-containing lactic acid bacterium is 20 ng or more per mg of dry bacterial cells.

(5) The production method according to any one of (1) to (4), wherein the lactic acid bacterium is at least one bacterium selected from the group consisting of lactic acid bacteria of the genus *Pediococcus*, lactic acid bacteria of the genus *Lactococcus*, lactic acid bacteria of the genus *Lactobacillus*, lactic acid bacteria of the genus *Streptococcus*, lactic acid bacteria of the genus *Leuconostoc*, and lactic acid bacteria of the genus *Tetragenococcus*.

(6) A method for suppressing a decrease in the content of double-stranded RNA in a lactic acid bacterium, including a step of culturing a lactic acid bacterium under at least one condition of an aeration condition and a low-temperature condition lower than an optimum temperature, thereby suppressing the decrease in the content of double-stranded RNA in the lactic acid bacterium.

(7) A method for screening for a double-stranded RNA-containing lactic acid bacterium, including a step of culturing a plurality of lactic acid bacteria under at least one condition of an aeration condition and a low-temperature condition lower than an optimum temperature, thereby screening for the double-stranded RNA-containing lactic acid bacterium.

(8) A double-stranded RNA-containing lactic acid bacterium, wherein the content of double-stranded RNA is 2.0 times or more as compared with the content of double-stranded RNA when a bacterium of the same strain is cultured for the same culture time under an optimum temperature and non-aeration condition.

(9) A double-stranded RNA-containing lactic acid bacterium, wherein the content of double-stranded RNA is 20 ng or more per mg of dry bacterial cells.

(10) The lactic acid bacterium according to (8) or (9), wherein the lactic acid bacterium is at least one bacterium selected from the group consisting of lactic acid bacteria of the genus *Pediococcus*, lactic acid bacteria of the genus *Lactococcus*, lactic acid bacteria of the genus *Lactobacillus*, lactic acid bacteria of the genus *Streptococcus*, lactic acid bacteria of the genus *Leuconostoc*, and lactic acid bacteria of the genus *Tetragenococcus*.

(11) A composition containing the lactic acid bacterium according to any one of (8) to (10).

(12) The composition according to (11), wherein the composition is one composition selected from the group consisting of a composition for food and drink, a composition for food and drink raw material, a composition for feed, and a composition for feed raw material.

Advantageous Effects of Invention

According to the method and the lactic acid bacterium of one embodiment of the present invention, a lactic acid bacterium having a high double-stranded RNA content can be efficiently obtained. In particular, the method of one embodiment of the present invention is a particularly remarkably excellent method for producing a lactic acid bacterium having a high double-stranded RNA content at an industrial scale. Further, according to the composition of one embodiment of the present invention, it can be expected that by the action of the double-stranded RNA-containing lactic acid bacterium contained therein, an individual who ingests the composition acquires innate immunity, and specifically, it can be expected that an antiviral effect, an immunostimulatory effect, an anti-infective effect, an anti-hepatitis B effect, an anti-hepatitis C effect, an antiproliferative effect, an antitumor effect, an anticancer effect, or the like is obtained.

An active ingredient used in the composition of one embodiment of the present invention is a material that has been proven for use as an additive or the like of foods and drinks. Therefore, the composition of one embodiment of the present invention is highly safe and is useful as an antiviral composition, an immunostimulatory composition, an anti-infective composition, an anti-hepatitis B composition, an anti-hepatitis C composition, an intestinal immunostimulatory composition, an airway immunostimulatory composition, an antitumor composition, an anticancer composition, or the like, and it can be expected that it is provided in an oral or parenteral form.

DESCRIPTION OF EMBODIMENTS

Hereinafter, a lactic acid bacterium, a composition, and a method that are one embodiment of the present invention will be described in detail, however, the technical scope of the present invention is not limited only to the matter of this item, and the present invention can adopt various embodiments as long as the object is achieved.

The lactic acid bacterium of one embodiment of the present invention is a lactic acid bacterium containing double-stranded RNA. The content of double-stranded RNA in the lactic acid bacterium of one embodiment of the present invention is 2.0 times or more, preferably 3.0 times or more, more preferably 5.0 times or more, further more preferably 10 times or more, still further more preferably 30 times or more as compared with the content of double-stranded RNA in a bacterium of the same strain when the bacterium is cultured for the same culture time under an optimum temperature and non-aeration condition. Further, the upper limit is not particularly limited, but is typically 1000 times or less.

Further, in the lactic acid bacterium of one embodiment of the present invention, when an evaluation method for double-stranded RNA as described in the below-mentioned Examples is adopted, the content of double-stranded RNA is preferably 20 ng or more per mg of dry bacterial cells, more preferably 50 ng or more per mg of dry bacterial cells, further more preferably 100 ng or more per mg of dry bacterial cells. Further, the upper limit is not particularly limited, but is typically 200 ng or less per mg of dry bacterial cells.

The lactic acid bacterium of one embodiment of the present invention can be obtained by culturing a lactic acid bacterium under a predetermined condition. The lactic acid bacterium used in this case means a microorganism that produces lactic acid as usually known.

Examples of the lactic acid bacterium include lactic acid bacteria belonging to lactic acid bacteria of the genus *Pediococcus*, lactic acid bacteria of the genus *Lactococcus*, lactic acid bacteria of the genus *Lactobacillus*, lactic acid bacteria of the genus *Streptococcus*, lactic acid bacteria of the genus *Leuconostoc*, lactic acid bacteria of the genus *Tetragenococcus*, and the like.

Specific examples thereof include, but are not limited to, *Pediococcus acidilactici, Lactococcus lactis, Lactobacillus plantarum, Lactobacillus pentosus, Lactobacillus sakei, Tetragenococcus halophilus, Pediococcus pentosaceus, Lactobacillus delbrueckii* ssp. *bulgaricus, Lactobacillus brevis, Lactobacillus casei* subsp. *casei, Lactobacillus paracasei* subsp. *paracasei, Lactobacillus rhamnosus, Streptococcus thermophilus, Leuconostoc mesenteroides* subsp. *mesenteroides, Leuconostoc pseudomesenteroides, Leuconostoc lactis*, and the like.

More specific non-limiting examples of the lactic acid bacterium include *Pediococcus acidilactici* K15 strain, *Lactococcus lactis* ATCC 19435 strain, *Lactobacillus plantarum* ATCC 14917 strain, *Lactobacillus pentosus* ATCC 8041 strain, *Lactobacillus* sakei K41 strain, *Tetragenococcus halophilus* KK221 strain, *Tetragenococcus halophilus* NBRC 12172 strain, *Pediococcus pentosaceus* OS strain (NITE P-354), *Pediococcus pentosaceus* NRIC 1915 strain, *Pediococcus pentosaceus* NRIC 0099 strain, *Pediococcus pentosaceus* NRIC 0122 strain, *Lactobacillus plantarum* NRIC 1930 strain, *Lactobacillus plantarum* NRIC 1067 strain, *Lactobacillus delbrueckii* subsp. *bulgaricus* NRIC 1688 strain, *Lactobacillus delbrueckii* subsp. *lactis* NRIC 1683 strain, *Lactobacillus brevis* NRIC 1713 strain, *Lactobacillus pentosus* NRIC 0391 strain, *Lactobacillus pentosus* NRIC 0396 strain, *Lactobacillus pentosus* NRIC 1836 strain, *Lactobacillus casei* subsp. *casei* NRIC 0644 strain, *Lactobacillus paracasei* subsp. *paracasei* NRIC 1936, *Streptococcus thermophilus* NRIC 0256 strain, *Leuconostoc mesenteroides* subsp. *mesenteroides* NRIC 1982 strain, *Leuconostoc* pseudomesenteroides ATCC 12291 strain, *Leuconostoc lactis* NRIC 1582 strain, *Lactobacillus delbrueckii* subsp. *bulgaricus* ATCC 11842 strain, *Lactobacillus rhamnosus* ATCC 53103 strain, and the like.

As the lactic acid bacterium used for obtaining the lactic acid bacterium of one embodiment of the present invention, among the above-mentioned lactic acid bacteria, one kind can be used alone or two or more kinds can be used in combination. Further, among the above-mentioned lactic acid bacteria, from the viewpoint of the content of double-stranded RNA, *Pediococcus acidilactici* K15 strain, *Lactococcus lactis* ATCC 19435 strain, *Lactobacillus plantarum* ATCC 14917 strain, *Lactobacillus pentosus* ATCC 8041 strain, *Lactobacillus* sakei K41 strain, *Lactobacillus delbrueckii* subsp. *bulgaricus* ATCC 11842 strain, and *Lactobacillus rhamnosus* ATCC 53103 strain are preferred, and *Pediococcus acidilactici* K15 strain is more preferred.

A method for obtaining the lactic acid bacterium is not particularly limited, and examples of the method include a method of utilizing a lactic acid bacterium that is commercially available or deposited, a method of separating a lactic acid bacterium from a lactic acid bacteria-containing material such as soy sauce moromi, a pickled product, or a commercially available lactic acid bacteria drink, and utilizing the separated bacterium, and the like. The optimum temperature for a general lactic acid bacterium is about 30° C. to 40° C., and for example, the optimum temperature for *Pediococcus acidilactici* K15 strain that is a lactic acid bacterial strain isolated from a salted rice bran bed is around 40° C., and the optimum temperature for *Lactobacillus* sakei K41 strain that is a lactic acid bacterial strain isolated from a pickled carrot is around 30° C.

The method of one embodiment of the present invention is a method for producing a double-stranded RNA-containing lactic acid bacterium such as the lactic acid bacterium of one embodiment of the present invention. The method for producing a double-stranded RNA-containing lactic acid bacterium of one embodiment of the present invention includes at least a step of culturing a lactic acid bacterium under an aeration condition, under a low-temperature condition lower than an optimum temperature, or under a low-temperature lower than an optimum temperature and aeration condition (hereinafter abbreviated as at least one condition of an aeration condition and a low-temperature condition lower than an optimum temperature), thereby obtaining the double-stranded RNA-containing lactic acid bacterium.

A method of another embodiment of the present invention is a method for suppressing a decrease in the content of double-stranded RNA in a lactic acid bacterium. The method for suppressing a decrease in the content of double-stranded RNA in a lactic acid bacterium of one embodiment of the present invention includes at least a step of culturing a lactic acid bacterium under at least one condition of an aeration condition and a low-temperature condition lower than an optimum temperature, thereby suppressing the decrease in the content of double-stranded RNA in the lactic acid bacterium.

A method of another embodiment of the present invention is a method for screening for a lactic acid bacterium capable of containing a large amount of double-stranded RNA from a plurality of lactic acid bacteria. The method for screening for a double-stranded RNA-containing lactic acid bacterium of one embodiment of the present invention includes at least a step of culturing a plurality of lactic acid bacteria under at least one condition of an aeration condition and a low-temperature condition lower than an optimum temperature, thereby screening for the double-stranded RNA-containing lactic acid bacterium.

The plurality of lactic acid bacteria refers to, for example, a plurality of strains of lactic acid bacteria, and specifically may be, for example, a plurality of different strains of lactic acid bacteria within a range of the same species, or may be a plurality of strains of lactic acid bacteria composed of different bacterial species. Specific examples of the screening step include a step of culturing a plurality of lactic acid bacteria under at least one condition of an aeration condition and a low-temperature condition lower than an optimum temperature, and screening for a lactic acid bacterium in which the content of double-stranded RNA is 2.0 times or more as compared with the content of double-stranded RNA in a bacterium of the same strain when the bacterium is cultured for the same culture time under an optimum temperature and non-aeration condition or the content of double-stranded RNA is 20 ng or more per mg of dry bacterial cells.

The method of one embodiment of the present invention is characterized by culturing a lactic acid bacterium under a condition different from a general condition for culturing a lactic acid bacterium such as at least one condition of an aeration condition and a low-temperature condition lower than an optimum temperature.

Examples of the culturing under an aeration condition include culturing under such a condition that a dissolved oxygen concentration is increased by supplying air and stirring or the like. At this time, oxygen gas may be used in place of air, and a means such as shaking other than stirring may be adopted as long as the dissolved oxygen concentration can be increased. Note that, the stirring rate can be appropriately set according to the size of a culture chamber or the like.

The supply amount of air (air flow rate) is not particularly limited, but is, for example, about 0.01 to 10 VVM, preferably about 0.1 to 1 VVM per unit volume. When the air flow rate is less than 0.01 VVM, the dissolved oxygen concentration may not be increased, and when the air flow rate is more than 10 VVM, the lactic acid bacterium may be physically damaged due to a large amount of air bubbles, and therefore, these cases are not preferred.

Examples of the culturing under a low-temperature condition lower than an optimum temperature include culturing under a condition where the temperature is lower than a temperature suitable for the proliferation of a lactic acid bacterium to be used, and the like. The low temperature lower than an optimum temperature is a temperature lower than the optimum temperature by 1° C. to 30° C., preferably a temperature lower than the optimum temperature by 5° C. to 20° C., more preferably a temperature lower than the optimum temperature by 5° C. to 15° C.

When the temperature at which the lactic acid bacterium is cultured is lower than the optimum temperature and a difference therebetween is 1° C. or more, an effect on the homeostasis of the lactic acid bacterium is suppressed, and the content of double-stranded RNA can be efficiently maintained or a decrease of the content can be suppressed. When the temperature at which the lactic acid bacterium is cultured is lower than the optimum temperature and a difference therebetween is 30° C. or less, a significant decrease in the survival or metabolic function of the lactic acid bacterium is suppressed, and a decrease in the yield of the lactic acid bacterium can be suppressed.

Note that, specifically, for example, the temperature lower than an optimum temperature by 1° C. to 30° C. means, when the optimum temperature for the lactic acid bacterium is 40° C., a temperature lower than 40° C. by 1° C. to 30° C., that is, 10° C. to 39° C.

The culturing under a low-temperature lower than an optimum temperature and aeration condition refers to culturing combining culturing under an aeration condition and culturing under a low-temperature condition lower than an optimum temperature. Specifically, for example, culturing under a condition where the temperature is lower than the optimum temperature by 1° C. to 30° C., and the air flow rate is about 0.01 to 10 VVM per unit volume, and the like are exemplified, and culturing under a condition where the temperature is lower than the optimum temperature by 5° C. to 15° C., and the air flow rate is about 0.1 to 1 VVM per unit volume is preferred.

The culturing of the lactic acid bacterium may be performed under a condition suitable for proliferation of the lactic acid bacterium to be used as another condition as long as the culturing is performed under at least one condition of an aeration condition and a low-temperature condition lower than an optimum temperature. For example, as a medium to be used, a medium generally used for culturing a lactic acid bacterium can be adopted. Examples of such a medium include, but are not limited to, an MRS medium, an M17 medium, and the like.

Specific examples of the method of one embodiment of the present invention include, but are not limited to, a method including a step of culturing any one kind or two or more kinds of lactic acid bacteria selected from the group consisting of lactic acid bacteria of the genus *Pediococcus*, lactic acid bacteria of the genus *Lactococcus*, lactic acid bacteria of the genus *Lactobacillus*, lactic acid bacteria of the genus *Streptococcus*, lactic acid bacteria of the genus *Leuconostoc*, and lactic acid bacteria of the genus *Tetragenococcus* for 10 to 30 hours using an MRS medium under at least one condition of a condition where the air flow rate is about 0.1 to 1 VVM per unit volume and a condition where the temperature is lower than the optimum temperature by 5° C. to 15° C., thereby obtaining a culture containing the double-stranded RNA-containing lactic acid bacterium, and the like.

In the method of one embodiment of the present invention, a culture time is not particularly limited as long as the culture time allows proliferation of the lactic acid bacterium to be observed, however, for example, it is preferably a time before the proliferation rate of the lactic acid bacterium decreases. For example, a time before the slope of a proliferation curve obtained by measuring an OD600 value of a culture of the lactic acid bacterium over time and then plotting the measured OD600 value against the culture time decreases can be referred to as the time before the proliferation rate of the lactic acid bacterium decreases.

In the method of one embodiment of the present invention, the content of double-stranded RNA in the lactic acid bacterium tends to decrease by culturing the lactic acid bacterium until when the proliferation rate of the lactic acid bacterium decreases, and therefore, the culture time is preferably set to a time before the proliferation rate of the lactic acid bacterium decreases. By referring to a proliferation curve at 40° C. in FIG. 2A, a specific example of the time before the proliferation rate of the lactic acid bacterium decreases can be a time before 6 hours after culturing, and more specifically, can be a time between 4 to 6 hours after culturing, or a time corresponding to 5 hours after culturing, but the culture time is not limited thereto.

In the method of one embodiment of the present invention, by culturing the lactic acid bacterium under at least one condition of an aeration condition and a low-temperature condition lower than an optimum temperature, the proliferation rate of the lactic acid bacterium can be decreased so as to facilitate the control of the culture time to the time before the proliferation rate of the lactic acid bacterium decreases, and therefore, the lactic acid bacterium that is made to contain a large amount of double-stranded RNA can be efficiently obtained in the end.

The method of one embodiment of the present invention may be a method including a step of pasteurizing the obtained culture, removing the medium by a generally known solid-liquid separation means such as an ultrafilter or a centrifugal concentrator so as to recover bacterial cells, and subsequently washing the obtained bacterial cells with water, a saline solution, or the like, thereby obtaining the bacterial cells of the lactic acid bacterium.

The thus obtained bacterial cells, a bacterial cell suspension in which the bacterial cells are suspended in water, a saline solution, or the like, a dry powder obtained by subjecting the bacterial cells to a drying treatment, or the like can be used as the double-stranded RNA-containing lactic acid bacterium. A method of the drying treatment is not particularly limited, and examples of the method include natural drying, air drying, spray drying, lyophilization, and the like.

In the method of one embodiment of the present invention, various steps or operations can be added before or after the above-mentioned steps, or during the steps, as long as the object of the present invention can be achieved.

The double-stranded RNA-containing lactic acid bacterium can be the lactic acid bacterium itself that is made to contain double-stranded RNA, that is, the bacterial cells of the lactic acid bacterium, and in addition thereto, a bacterial component of the lactic acid bacterium, a culture of the lactic acid bacterium, and the like. The bacterial cells, the bacterial component, and the culture of the double-stranded RNA-containing lactic acid bacterium can also be said to be an immunoregulatory material, an immunostimulatory material, and an antiallergic material due to the action of regulating, stimulating, suppressing, and optimizing the immunity of the double-stranded RNA contained therein.

Examples of the bacterial cells of the lactic acid bacterium include bacterial cells obtained by removing the medium from a culture of the lactic acid bacterium by using a generally known solid-liquid separation means such as centrifugation, and the like. Examples of the bacterial component include a purified or unpurified component which is present inside the bacterial cells of the lactic acid bacterium, or which is secreted outside the bacterial cells. Specific examples of the bacterial component include components containing single-stranded RNA, single-stranded DNA, double-stranded DNA, or the like as well as double-stranded RNA, and the like. Examples of the culture of the lactic acid bacterium include a culture solution itself obtained by culturing the lactic acid bacterium, and the like.

The bacterial cells, the bacterial component, and the culture as the double-stranded RNA-containing lactic acid bacterium can be any one kind thereof alone or a combination of two or more kinds thereof. For example, they may be a material obtained by isolating double-stranded RNA from the bacterial cells, the bacterial component, and the culture of the double-stranded RNA-containing lactic acid bacterium. A method for isolating double-stranded RNA from the bacterial cells, the bacterial component, and the culture of the double-stranded RNA-containing lactic acid bacterium is not particularly limited, however, examples thereof include a method described in Japanese Patent No. 5312322, and the like.

Specific examples of the method for isolating double-stranded RNA from the double-stranded RNA-containing lactic acid bacterium include, for example, the following method, and the like. That is, the double-stranded RNA-containing lactic acid bacterium is subjected to a heat and pasteurization treatment at 90 to 100° C. for 5 to 20 minutes, thereby obtaining a heat and pasteurization-treated liquid.

Subsequently, the heat and pasteurization-treated liquid is subjected to a solid-liquid separation means such as centrifugation, and solid contents are recovered. Subsequently, the solid contents are washed and suspended in a buffer solution, thereby obtaining a suspension. Subsequently, lysozyme is added to the suspension, followed by warming to 35 to 40° C., thereby obtaining a lysozyme-treated solution.

Subsequently, SDS and Proteinase K are added to the lysozyme-treated solution, followed by warming to 35 to 40° C., thereby obtaining a proteinase-treated solution. Subsequently, the proteinase-treated solution is treated with phenol-chloroform-isoamyl alcohol, and then subjected to a solid-liquid separation means such as centrifugation, thereby obtaining a crude nucleic acid extract as a supernatant. The crude nucleic acid extract is a nucleic acid mixture containing DNA, single-stranded RNA, double-stranded RNA, or the like.

Subsequently, by subjecting the crude nucleic acid extract to cellulose column chromatography, purified double-stranded RNA can be obtained. The cellulose column chromatography and the subsequent advanced purification means can be carried out according to the description of Japanese Patent No. 5312322.

In the method of one embodiment of the present invention, the content of double-stranded RNA in the double-stranded RNA-containing lactic acid bacterium is preferably 2.0 times or more, more preferably 3.0 times or more, further more preferably 5.0 times or more, particularly preferably 10 times or more, and most preferably 30 times or more as compared with the content of double-stranded RNA when a bacterium of the same strain is cultured for the same culture time under an optimum temperature and non-aeration condition. Further, the upper limit is not particularly limited, but is typically 1000 times or less.

In the method of one embodiment of the present invention, when an evaluation method for double-stranded RNA as described in the below-mentioned Examples is adopted, the content of double-stranded RNA in the double-stranded RNA-containing lactic acid bacterium is preferably 20 ng or more per mg of dry bacterial cells, more preferably 50 ng or more per mg of dry bacterial cells, further more preferably 100 ng or more per mg of dry bacterial cells. Further, the upper limit is not particularly limited, but is typically 200 ng or less per mg of dry bacterial cells.

The composition of one embodiment of the present invention contains at least the double-stranded RNA-containing lactic acid bacterium of one embodiment of the present invention. It is expected that the double-stranded RNA-containing lactic acid bacterium exhibits an antiviral effect, an immunostimulatory effect, an anti-infective effect, an anti-hepatitis B effect, an anti-hepatitis C effect, an antiproliferative effect, an antitumor effect, an anticancer effect, and the like. Therefore, the composition of one embodiment of the present invention can adopt an embodiment of an antiviral composition, an immunostimulatory composition, an anti-infective composition, an anti-hepatitis B composition, an anti-hepatitis C composition, an intestinal immunostimulatory composition, an airway immunostimulatory composition, an antitumor composition, or an anticancer composition.

An anti-disease effect that can be exhibited by the composition of one embodiment of the present invention means that, for example, in the case of an antiviral effect, a current or future viral disease in an individual who ingests the composition or a state where the individual is considered to have caught a viral disease is suppressed, slowed down, or the state is improved. An immunostimulatory effect exhibited by the composition of one embodiment of the present invention means that, for example, the current or future immune system in an individual who ingests the composition is activated so as to recover various diseases or abnormalities to a normal state.

The double-stranded RNA-containing lactic acid bacterium is a proven natural product or a derived material thereof, which has been ingested by humans or animals for a long period of time, and thus is highly safe, and therefore, the composition of one embodiment of the present invention has high practicality, and can be applied in various applications in an oral or parenteral form by itself alone or by being processed together with another composition, or by being added to another composition.

A specific embodiment of the composition of one embodiment of the present invention is not particularly limited, and examples thereof include foods and drinks, animal feed, cosmetics, pharmaceuticals, quasi-drugs, and raw materials or raw material compositions for producing these products, and the like, however, from the viewpoint of ease of daily ingestion by an individual who ingests the composition, it is preferably a composition for food and drink, a composition for food and drink raw material, a composition for feed, and a composition for feed raw material, and more preferably a functional food and drink, a food and drink for a specified health use, a nutritional functional food and drink, a health functional food and drink, a food and drink for a special purpose, a nutritional supplement food and drink, a health supplement food and drink, a supplement, a beauty food and drink, and a raw material or a raw material composition for producing such a product.

The composition of one embodiment of the present invention can be, for example, used by being mixed with another component as needed. As described above, in the composition of one embodiment of the present invention, various materials can be blended in addition to the double-stranded RNA-containing lactic acid bacterium as long as the object of the present invention can be achieved.

In the composition of one embodiment of the present invention, for example, an additive used for general food processing such as a sugar sweetener, a stabilizer, an emulsifier, a starch, a processed starch product, a hydrolyzed starch product, dietary sodium chloride, a flavoring agent, a coloring agent, an acidulant, a flavor ingredient, a nutrient, a fruit juice, an animal or vegetable food ingredient such as an egg, an excipient, a bulking agent, a binder, a thickener, or a flavoring oil can be further contained. A used amount of the additive is not particularly limited as long as the achievement of the object of the present invention is not hindered, and the amount can be appropriately set.

The composition of one embodiment of the present invention is not particularly limited as long as it is in a generally used form, and for example, the composition can adopt various forms such as a solid form, a liquid form, a gel form, a suspension form, a cream form, a sheet form, a stick form, a powder form, a particle form, a granule form, a tablet form, a rod form, a plate form, a block form, a paste form, a capsule form, and a caplet form.

In the case where the composition of one embodiment of the present invention is, for example, an oral composition, the composition is preferably an enteric-coated composition capable of delivering double-stranded RNA isolated from the double-stranded RNA-containing lactic acid bacterium to the small intestine through the esophagus and the stomach. The enteric-coated composition is not particularly limited as long as it is a composition in a form that is not dissolved by gastric acid but is dissolved in the small intestine, and examples of the enteric-coated composition include a composition in a form of an acid-resistant microcapsule or a liposome, and the like.

The content of the double-stranded RNA-containing lactic acid bacterium contained in the composition of one embodiment of the present invention is not particularly limited as long as the content allows the expected effect to be observed. In the case of an oral composition, the content thereof is, for example, 0.0001 mass % or more, preferably 0.001 mass % or more with respect to the entire composition. In the case of a parenteral composition, the content thereof is, for example, 0.00001 mass % or more, preferably 0.0001 mass % or more. The ingestion amount of the composition of one embodiment of the present invention is not particularly limited and may be appropriately set according to the symptoms or the body constitution of an individual who ingests the composition, but is, for example, 1 to 1000 mg/60 kg of body weight/day, or the like.

Hereinafter, the present invention will be described in more detail by way of Examples, but the present invention is not limited to these Examples, and can adopt various embodiments as long as the object of the present invention can be achieved.

EXAMPLES

Example 1. Evaluation of Amount of Double-Stranded RNA in Lactic Acid Bacterium Under Aeration Condition The amount of double-stranded RNA when a lactic acid bacterium was cultured under an aeration condition was evaluated.

An MRS medium (manufactured by Becton, Dickinson and Company) was inoculated with *Pediococcus acidilactici* K15 strain [hereinafter also referred to as K15 strain, Front Immunol. 2018 Jan. 23; 9: 27. doi: 10.3389/fimmu.2018.00027. eCollection 2018, and Sci Rep. 2018 Mar. 22; 8(1): 5065. doi: 10.1038/s41598-018-23404-4] or *Lactococcus lactis* ATCC 19435 strain (hereinafter also referred to as ATCC 19435 strain) at a cell density of $1 \times 10^7$ cells/mL, whereby a lactic acid bacterial stock solution was prepared. A 100-mL portion of the obtained lactic acid bacterial stock solution was cultured at 31° C. for 13 hours under an aeration condition where the air flow rate per unit volume was set to 0.5 VVM using a 200-mL culture chamber. At this time, a test group in which stirring was performed at 500 rpm and a test group in which culturing was performed at 31° C. while stirring at 100 rpm without aeration as a control were provided.

The culture solution was recovered after 13 hours from the start of culturing and then subjected to a boiling and pasteurization treatment at 95° C. for 15 minutes, whereby a pasteurization-treated solution was prepared. The bacterial cells obtained by centrifuging the prepared pasteurization-treated solution were washed with a physiological saline solution, followed by centrifugation again, and the thus obtained bacterial cells were lyophilized.

A 5-mg portion of the obtained lyophilized powder was suspended in a STE buffer, whereby a suspension was obtained. To the obtained suspension, a lysozyme solution (final concentration: 5 mg/mL) prepared by suspending lysozyme (Sigma-Aldrich Co. LLC.) in a STE buffer was added, followed by warming to 37° C. for 30 minutes, whereby a lysozyme-treated solution was obtained.

To the obtained lysozyme-treated solution, 10% SDS (Wako Pure Chemical Industries, Ltd.) and Proteinase K (Takara Bio Inc.) were added, followed by warming to 37° C. for 1 hour, whereby a proteinase-treated solution was obtained. The obtained proteinase-treated solution was treated with phenol-chloroform-isoamyl alcohol (Wako Pure Chemical Industries, Ltd.), followed by centrifugation at 8500×g for 15 minutes, whereby a crude nucleic acid extract was obtained as a supernatant.

Figure 1A:
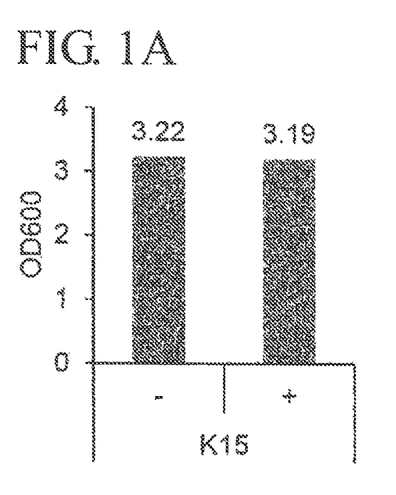
FIGS. 1A and 1B are graphs showing results of measuring OD600 values of various lactic acid bacteria when they were cultured under a non-aeration condition or an aeration condition described in the below-mentioned Examples.
Figure 1B:
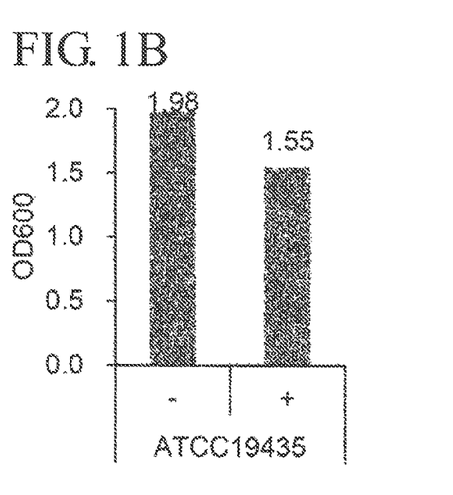
Figure 1C:
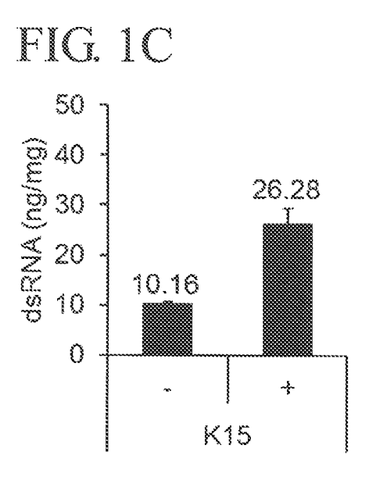
FIGS. 1C and 1D are graphs showing results of measuring the amount of double-stranded RNA in various lactic acid bacteria when they were cultured under a non-aeration condition or an aeration condition described in the below-mentioned Examples. In the graphs, (−) shows the results when the culturing was performed without aeration, and (+) shows the results when the culturing was performed under an aeration condition.
Figure 1D:
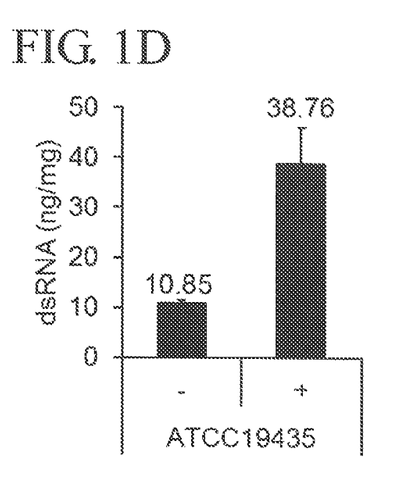

From the obtained crude nucleic acid extract, double-stranded RNA was quantitatively determined by the ELISA method. The amount of double-stranded RNA obtained by measurement is shown in FIGS. 1C and 1D. Further, the results of measuring OD of respective culture solutions are shown in FIGS. 1A and 1B. Note that OD600 is an absorbance at 600 nm and is the turbidity of a culture solution. A condition for providing a high OD600 can be said to be a condition suitable for proliferation of a lactic acid bacterium.

As shown in FIGS. 1C and 1D, it was confirmed that when the culturing was performed under the aeration condition, the amount of double-stranded RNA in the K15 strain and the ATCC 19435 strain was increased as compared with the case where the culturing was performed under the non-aeration condition.

Note that when the stirring rate was set to 300 rpm and the culture time was set to 18 hours so as to increase the yield of the double-stranded RNA-containing lactic acid bacterium, it was confirmed that the content of double-stranded RNA in the bacterial cells was extremely decreased. Accordingly, it was found that in order to increase the yield of the double-stranded RNA-containing lactic acid bacterium, it is important to obtain a lactic acid bacterium in a state where the content of double-stranded RNA in the bacterial cells is increased by controlling the culture condition such as the culture time.

Example 2. Evaluation of Amount of Double-Stranded RNA in Lactic Acid Bacterium of Genus *Pediococcus* Under Various Culture Temperature Conditions The amount of double-stranded RNA when a lactic acid bacterium belonging to the genus *Pediococcus* was cultured at various culture temperatures was evaluated.

An MRS medium was inoculated with K15 strain at a cell density of $1\times10^7$ cell s/mL, whereby a lactic acid bacterial stock solution was prepared. Note that the optimum temperature for the K15 strain was around 40° C. as described above.

The prepared lactic acid bacterial stock solution was statically cultured at 25° C., 31° C., and 40° C. for 22 hours, and OD600 was measured at a plurality of time points. The values of OD600 obtained by measurement are shown in FIG. 2A.

When the culturing was performed at 25° C., the culture solution was recovered at the 10th, 14th, and 22nd hours, when the culturing was performed at 31° C., the culture solution was recovered at the 8th, 13th, and 14th hours, and when the culturing was performed at 40° C., the culture solution was recovered at the 4th, 6th, and 14th hours, and the recovered culture solutions were subjected to a boiling and pasteurization treatment at 95° C. for 15 minutes, whereby pasteurization-treated solutions were prepared. The bacterial cells obtained by centrifuging each of the prepared pasteurization-treated solutions were washed with a physiological saline solution, followed by centrifugation again, and the thus obtained bacterial cells were lyophilized.

From a 5-mg portion of the obtained lyophilized powder, crude nucleic acid extraction and measurement of the amount of double-stranded RNA were performed in the same manner as in Example 1. The amount of double-stranded RNA obtained by measurement is shown in FIG. 2B.

Figure 2A:
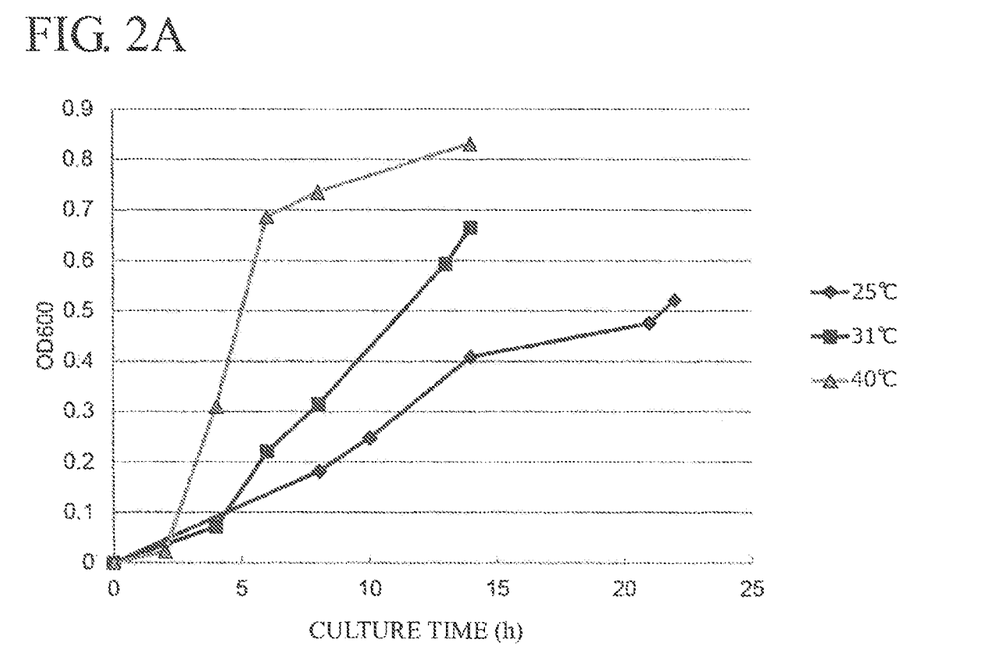
FIG. 2A is a graph showing results of measuring OD600 values of K15 strain when it was cultured at various temperatures described in the below-mentioned Examples.
Figure 2B:
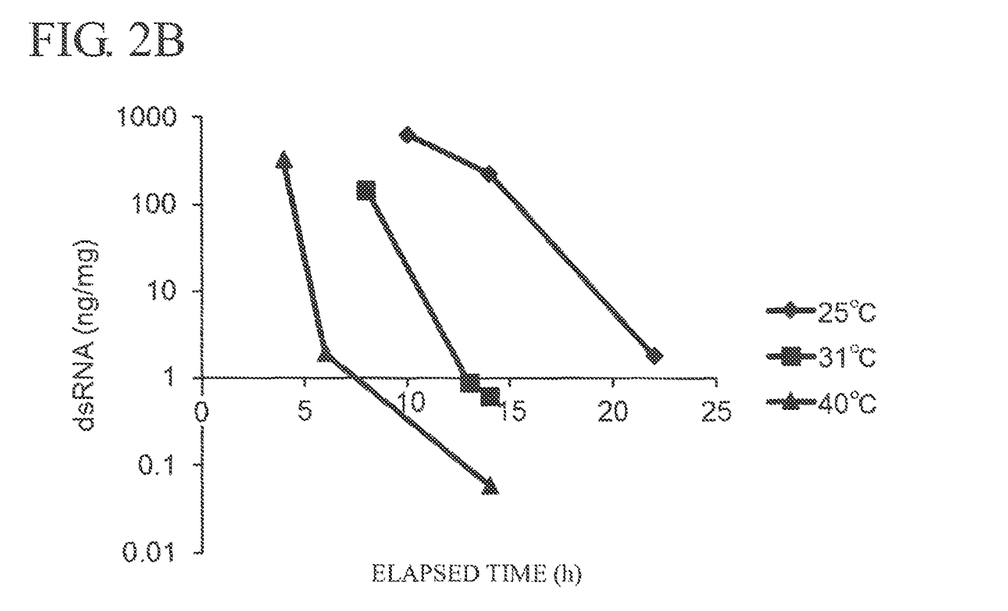
FIG. 2B is a graph showing results of measuring the amount of double-stranded RNA in K15 strain when it was cultured at various temperatures described in the below-mentioned Examples.

As shown in FIGS. 2A and 2B, it was found that although a large fluctuation in the maximum value of the content of double-stranded RNA due to the culture temperature was not observed, when the culturing was performed at 25° C. and 31° C., each of which is a low-temperature condition lower than the optimum temperature, the proliferation rate of bacterial cells can be reduced as compared with the case where the culturing was performed at 40° C. that is the optimum temperature, and the rate of decrease in the content of double-stranded RNA in bacterial cells can be mitigated accompanying this. From these results, it was found that in order to obtain the double-stranded RNA-containing lactic acid bacterium at an industrial scale, it is preferred to culture the lactic acid bacterium under a low-temperature condition lower than the optimum temperature.

Example 3. Evaluation of Amount of Double-Stranded RNA in Lactic Acid Bacterium of Genus *Pediococcus* Under Low-Temperature Condition Lower than Optimum Temperature and Aeration Condition The amount of double-stranded RNA when a lactic acid bacterium belonging to the genus *Pediococcus* was cultured under a low-temperature condition lower than the optimum temperature and an aeration condition was evaluated.

An MRS medium was inoculated with K15 strain at a cell density of $1\times10^7$ cell s/mL, whereby a lactic acid bacterial stock solution was prepared. A test group in which a 100-mL portion of the prepared lactic acid bacterial stock solution was statically cultured at 40° C. that is the optimum temperature for 14 hours using a 200-mL culture chamber was provided. Further, a test group in which a 100-mL portion of the lactic acid bacterial stock solution was cultured at 25° C. for 16 hours while stirring at 300 rpm under an aeration condition where the air flow rate per unit volume was set to 0.5 VVM using a 200-mL culture chamber was provided.

The culture solution was recovered after the culturing and then subjected to a boiling and pasteurization treatment at 95° C. for 15 minutes, whereby a pasteurization-treated solution was prepared. The bacterial cells obtained by centrifuging the prepared pasteurization-treated solution were washed with a physiological saline solution, followed by centrifugation again, and the thus obtained bacterial cells were lyophilized.

From a 5-mg portion of the obtained lyophilized powder, crude nucleic acid extraction and measurement of the amount of double-stranded RNA were performed in the same manner as in Example 1. The amount of double-stranded RNA obtained by measurement is shown in FIG. 3.

Figure 3:
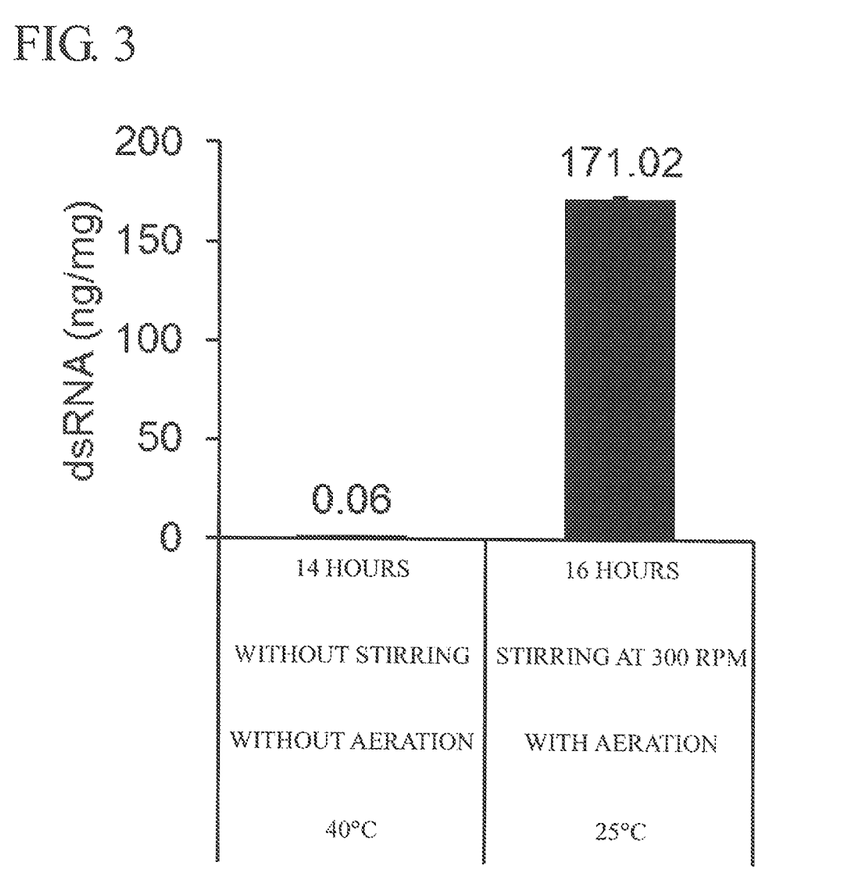
FIG. 3 is a graph showing results of measuring the amount of double-stranded RNA in K15 strain when it was cultured under an aeration and low-temperature condition described in the below-mentioned Examples.

As shown in FIG. 3, it was confirmed that when the culturing was performed under the aeration condition and the low-temperature condition lower than the optimum temperature, the amount of double-stranded RNA in the bacterial cells becomes a high value as compared with the case where the culturing was performed under the non-aeration condition and the optimum temperature condition.

Example 4. Evaluation of Amount of Double-Stranded RNA in Lactic Acid Bacterium of Genus *Lactobacillus* Under Aeration Condition The amount of double-stranded RNA when a lactic acid bacterium was cultured under an aeration condition was evaluated.

An MRS medium (manufactured by Becton, Dickinson and Company) was inoculated with *Lactobacillus delbrueckii* subsp. *bulgaricus* ATCC 11842 strain (hereinafter also referred to as ATCC 11842 strain), or *Lactobacillus rhamnosus* ATCC 53103 strain (hereinafter also referred to as LGG strain, LGG is registered trademark) at a cell density of $1\times10^7$ cells/mL, whereby a lactic acid bacterial stock solution was prepared. A 100-mL portion of the obtained lactic acid bacterial stock solution was cultured at 37° C. for 10 hours in the case of the ATCC 11842 strain and at 37° C. for 9 hours in the case of the LGG strain under an aeration condition where the air flow rate per unit volume was set to 0.5 VVM using a 200-mL culture chamber. At this time, a test group in which stirring was performed at 500 rpm and a test group in which the culturing was performed while stirring at 100 rpm without aeration as a control were provided.

After completion of the culturing, the culture solution was recovered and then subjected to a boiling and pasteurization treatment at 95° C. for 15 minutes, whereby a pasteurization-treated solution was prepared. The bacterial cells obtained by centrifuging the prepared pasteurization-treated solution were washed with a physiological saline solution, followed by centrifugation again, and the thus obtained bacterial cells were lyophilized.

A 5-mg portion of the obtained lyophilized powder was suspended in a STE buffer, whereby a suspension was obtained. To the obtained suspension, a lysozyme solution (final concentration: 5 mg/mL) prepared by suspending lysozyme (Sigma-Aldrich Co. LLC.) in a STE buffer was added, followed by warming to 37° C. for 30 minutes, whereby a lysozyme-treated solution was obtained.

To the obtained lysozyme-treated solution, 10% SDS (Wako Pure Chemical Industries, Ltd.) and Proteinase K (Takara Bio Inc.) were added, followed by warming to 37° C. for 1 hour, whereby a proteinase-treated solution was obtained. The obtained proteinase-treated solution was treated with phenol-chloroform-isoamyl alcohol (Wako Pure Chemical Industries, Ltd.), followed by centrifugation at 8500×g for 15 minutes, whereby a crude nucleic acid extract was obtained as a supernatant.

Figure 4A:
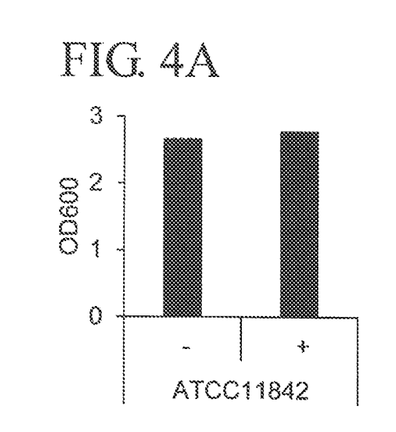
FIGS. 4A and 4B are graphs showing results of measuring OD600 values of various lactic acid bacteria when they were cultured under a non-aeration condition or an aeration condition described in the below-mentioned Examples.
Figure 4B:
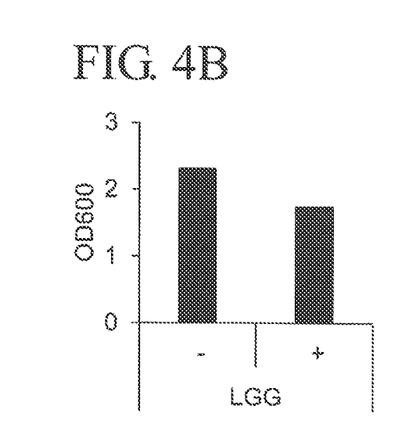
Figure 4C:
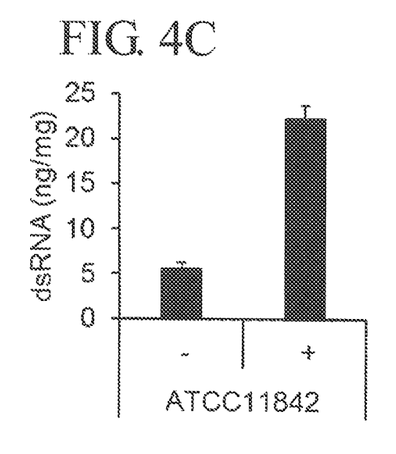
FIGS. 4C and 4D are graphs showing results of measuring the amount of double-stranded RNA in various lactic acid bacteria when they were cultured under a non-aeration condition or an aeration condition described in the below-mentioned Examples. In the graphs, (−) shows the results when the culturing was performed without aeration, and (+) shows the results when the culturing was performed under an aeration condition.
Figure 4D:
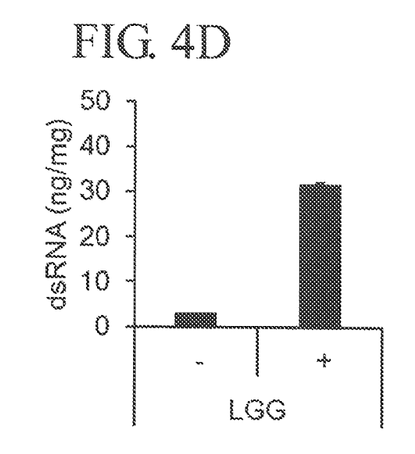

From the obtained crude nucleic acid extract, double-stranded RNA was quantitatively determined by the ELISA method. The amount of double-stranded RNA obtained by measurement is shown in FIGS. 4C and 4D. Further, the results of measuring OD of respective culture solutions are shown in FIGS. 4A and 4B.

As shown in FIGS. 4C and 4D, it was confirmed that when the culturing was performed under the aeration condition, the amount of double-stranded RNA in the ATCC 11842 strain and the LGG strain was increased as compared with the case where the culturing was performed under the non-aeration condition.

From the above results, it could be confirmed that by culturing various lactic acid bacteria under at least one condition of an aeration condition and a low-temperature condition lower than an optimum temperature, a lactic acid bacterium having a high double-stranded RNA content is efficiently obtained.

Although the present invention has been described in detail using the specific embodiments, it is apparent to those skilled in the art that various modifications and variations are possible without departing from the spirit and scope of the present invention. Note that the present application is based on a Japanese patent application (Japanese Patent Application No. 2017-095947) filed on May 12, 2017, the entirety of which is incorporated herein by reference.

INDUSTRIAL APPLICABILITY

The lactic acid bacterium and the composition of one embodiment of the present invention and a lactic acid bacterium and a composition obtained by the method of one embodiment of the present invention contain double-stranded RNA and contribute to the innate immune cell response, and therefore are useful for an individual who ingests such a material in expectation of an antiviral activity, an immunostimulatory activity, an anti-infective activity, an anti-hepatitis B activity, an anti-hepatitis C activity, an antiproliferative activity, an antitumor activity, or an anti-cancer activity, and can be utilized as a food and drink, a pharmaceutical, a quasi-drug, a cosmetic, a supplement, and the like that contribute to the health and welfare of an individual who ingests such a material.

The invention claimed is:

1. A double-stranded RNA-containing lactic acid bacterium,
wherein the content of double-stranded RNA of said lactic acid bacterium is 20 ng or more per mg of dry bacterial cells.

2. The double-stranded RNA-containing lactic acid bacterium of claim 1,
wherein the content of double-stranded RNA of said lactic acid bacterium is 50 ng or more per mg of dry bacterial cells.

3. The double-stranded RNA-containing lactic acid bacterium of claim 1,
wherein the content of double-stranded RNA of said lactic acid bacterium is 100 ng or more per mg of dry bacterial cells.

4. The double-stranded RNA-containing lactic acid bacterium of claim 1,
wherein the content of double-stranded RNA of said lactic acid bacterium is 200 ng or less per mg of dry bacterial cells.

5. The double-stranded RNA-containing lactic acid bacterium of claim 2,
wherein the content of double-stranded RNA of said lactic acid bacterium is 200 ng or less per mg of dry bacterial cells.

6. The double-stranded RNA-containing lactic acid bacterium of claim 3,
wherein the content of double-stranded RNA of said lactic acid bacterium is 200 ng or less per mg of dry bacterial cells.

* * * * *